United States Patent [19]

Holtkamp

[11] Plant 5,170

[45] Jan. 3, 1984

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "OPTIMARA", Isselburg, Fed. Rep. of Germany

[21] Appl. No.: 300,629

[22] Filed: Sep. 9, 1981

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet named Rhode Island having intensive pink flower color, with a somewhat deeper pink tone in the center, and frilled edges. The variety is profuse in bloom, with up to 15 flower stems each carrying up to 12 or more flowers per stem. The growth is uniform, the leaves dark green and shiny, and the flowers long lasting and non-dropping. The plant is saleable within 8 weeks after potting.

1 Drawing Figure

The present invention comprises a new and distinct cultivar of African violet plant, botanically known as *Saintpaulia ionantha,* and hereinafter referred to by the cultivar name Rhode Island.

The new cultivar was referred to during the breeding and selection process by the designation d 29/23, and is a product of a planned breeding program. The basic objective of the breeding program was to create a new African violet cultivar having intensive pink flower color with frilled petal edges.

The new cultivar was originated from a cross made in a controlled breeding program in Isselburg, West Germany. The female, or seed parent was a cultivar designated b 244/10 pink. The male, or pollen parent was a cultivar designated b 16/6 pink frilled.

The new cultivar Rhode Island was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Rhode Island has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Rhode Island, which in combination distinguish this African violet as a new and distinct cultivar:

1. Intensive pink flower with deeper tone in center, and filled edges.
2. Mature flowers darker in color, returning to pink when old.
3. Profuse and fluffy in bloom; older flower stems bend to tilt sidewards to make space for upcoming younger flowers from center.
4. Up to 15 flower stems, carrying between 5–12 or more flowers per stem.
5. Uniform in growth.
6. Saleable within 8 weeks after potting.
7. Dark green shiny leaves.
8. Long lasting and non-dropping flowers.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany. It is noted that the color reproduction tends toward pink rather than pinkish purple, although the true color appears in the veining of the flowers. The color values stated below are correct.

Botanical classification: *Saintpaulia ionantha,* Ramat. cv. Rhode Island.

Parentage:

*Male parent.*—b 16/6 pink frilled.

*Female parent.*—b 244/10 pink.

Propagation: The new cultivar holds its distinguishing characteristics through successive propagations by leaf cuttings and by division of shoots.

Plant: Up to 10 cm. tall when grown in pots, and approximately 25–30 cm. in diameter when fully grown.

Leaves:

*General form.*—Heart-shaped.

*Diameter.*—60–70 mm.

*Texture.*—Soft and slightly hairy.

*Aspect.*—Dark and shiny.

*Veins.*—Upperside slightly visible; underside, well-pronounced, light green to brown and hairy.

*Color (upperside).*—HCC ivy green 0001060.

*Color (underside).*—HCC approaching dahlia purple 3939/1.

*Petiole.*—Young petiole purplish brown; old petiole less intensive.

Flowers:

*Buds.*—Ball-shaped; 6 mm. just before opening; 5–12 or more per stem.

*Sepals.*—Color: Greenish brown. Calyx: Flat, funneled. Aspect: Spear-shaped with rounded-off tip. Peduncle: Short, strong and sturdy, tilted, greenish brown to brown.

Individual flowers:

*Size.*—40 mm.

*Color.*—Upperside: Cyclamen purple 30/3; center somewhat lighter than 30/2; true color shows in the veining, with the flowers otherwise being depicted as somewhat more pink than they really are. Underside: Cyclamen purple 30/3.

*Borne.*—Flower stem carries 5–12 or more short, strong, upright peduncles; basically single flowering, occasionally a sixth petal.

*Shape.*—Conventional (2 small and 3 large petals.

Flowering time; First flowers appear 6–7 weeks after potting; after 8–10 weeks full flowering saleable plant.

Reproductive organs:

*Stamens.*—2 anthers, composed of 2 cells, with seed capsule slightly pushed through.

*Anthers.*—Aureolin 3

*Filaments.*—3 mm. long; yellowish green and purple stripes.

*Styles.*—7 mm. reddish green; base of ovary light green, hairy.

*Pollen color.*—HCC sulphur yellow 1/3.

Roots: White when young and active; greenish brown when older; normally developed.

Disease resistance: Good as experienced to date.

General observations: Rhode Island has remarkably dark green shiny leaves with a distinct purple underside for young and old leaves. Its corolla is fluffy and profuse in bloom, flowering continuously, with intense pink flower color. Its flowers do not fade, and are long-lasting and non-dropping as they dry off on the stem after full maturity. When opening, the young flower is pale pink, then changes into an intensive pink with a deeper center.

I claim:

1. A new and distinct cultivar of African violet plant known by the cultivary name Rhode Island and particularly characterized by the combined features of intensive pink flower color, with a somewhat darker pink center; profuse blooming habit providing a corolla which appears rather fluffy during full bloom; dark green shiny leaves; excellent growth habit, producing up to 15 flower stems, each of which contains up to 12 or more flowers per stem, with the flowers being long lasting and non-dropping, and by its ability to provide a saleable plant within 8 weeks after potting.

* * * * *

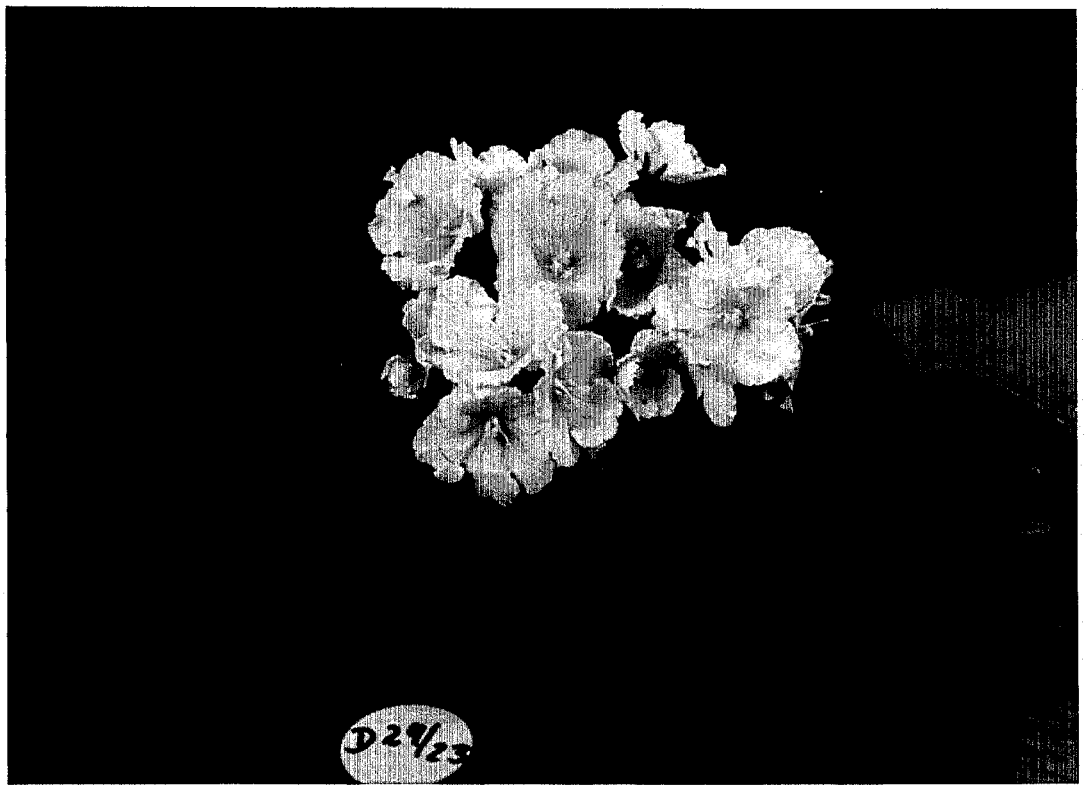
D29/25

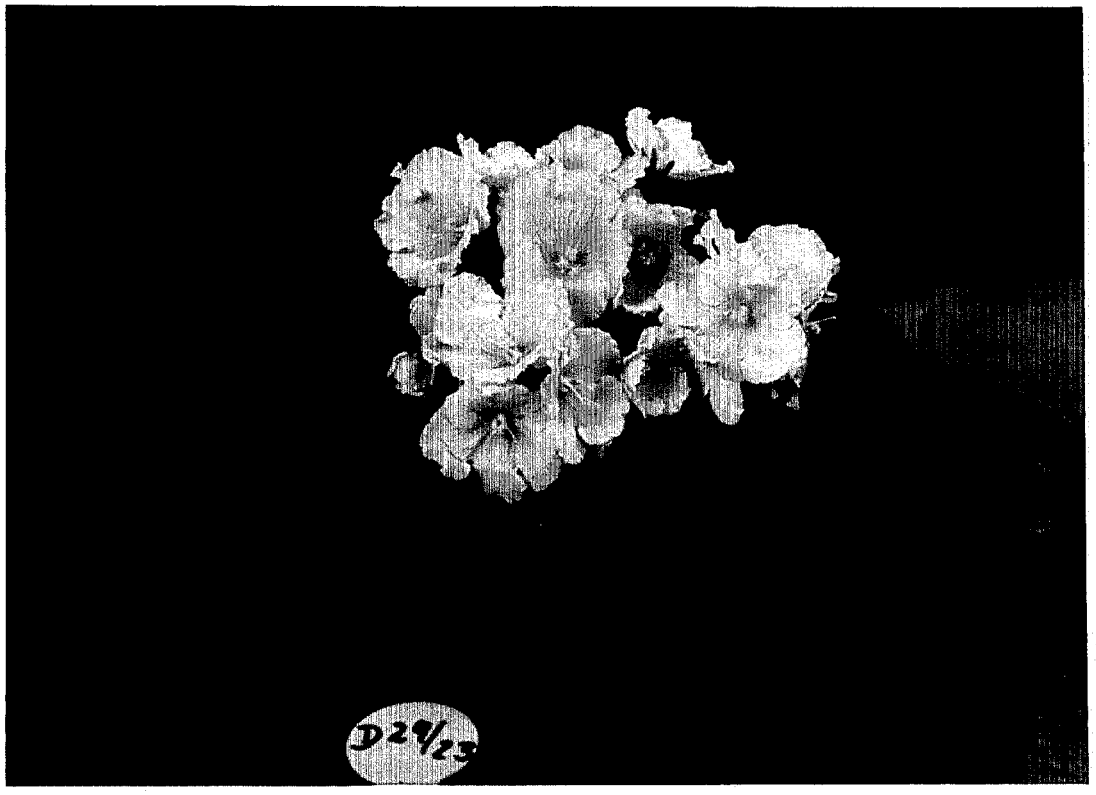
D29/25